United States Patent [19]
deSolms et al.

[11] Patent Number: 5,491,164
[45] Date of Patent: Feb. 13, 1996

[54] INHIBITORS OF FARNESYL-PROTEIN TRANSFERASE

[75] Inventors: S. Jane deSolms, Norristown; Samuel J. Graham, Schwenksville, both of Pa.

[73] Assignee: Merck & Co., Inc., Rahway, N.J.

[21] Appl. No.: 315,151

[22] Filed: Sep. 29, 1994

[51] Int. Cl.$^6$ ............... A61K 38/05; C07D 207/06; C07D 207/08; C07D 207/09

[52] U.S. Cl. .............. 514/423; 514/307; 514/314; 514/326; 514/343; 514/365; 514/397; 514/414; 514/422; 514/424; 514/426; 514/428; 546/281; 546/208; 546/174; 546/181; 546/146; 546/148; 546/151; 548/537; 548/544; 548/546; 548/557; 548/558; 548/569; 548/314.7; 548/518

[58] Field of Search ................... 548/569, 537, 548/534, 544, 546, 557, 558; 514/428, 423, 424, 426

[56] References Cited

U.S. PATENT DOCUMENTS

| | | | |
|---|---|---|---|
| 4,746,676 | 5/1988 | Neiss et al. | 514/423 |
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,326,773 | 7/1994 | de Solms et al. | 514/336 |
| 5,340,828 | 8/1994 | Graham et al. | 514/357 |
| 5,352,705 | 10/1994 | Deana et al. | 514/630 |

FOREIGN PATENT DOCUMENTS

| | | |
|---|---|---|
| 0456180A1 | 11/1991 | European Pat. Off. |
| 0618221A2 | 10/1994 | European Pat. Off. |
| WO91/16340 | 10/1991 | WIPO |

OTHER PUBLICATIONS

Akhrem et al. CA(87:23717z) p. 698 1977 and Formula Index.

Choi, S. H.; Yu, J. Y.; Shin, J. K. and Jhon, M. S. J. of Mol. Struct. Jul. 1994 323(1–3) pp. 233–242.

Akhrem et al. Dokl. Akad. Nauk BSSR 1977 21(1) pp. 38–41.

Gibbs, J. B. et al., "Selective Inhibition of Farnesyl–Protein Transferase Blocks Ras Processing in Vivo", The Journal of Biological Chemistry, vol. 268, No. 11, pp. 7617–7620 (Apr. 1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (Aug. 1991).

James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (Nov. 1994).

James, G. L. et al., "Benzodiazepine Peptidomimetics: Potent Inhibitors of Ras Farnesylation in Animal Cells", Science, vol. 260, pp. 1937–1942 (Jun. 1993).

Kohl, N. E. et al., "Selective Inhibition of ras–Dependent Transformation by a Farnesyltransferase Inhibitor", Science, vol. 260, pp. 1934–1937 (Jun. 1993).

Kohl, N. E. et al., "Protein farnesyltransferase inhibitors block the growth of ras–dependent tumors in nude mice", Proc. Natl. Acad. Sci. USA, Med. Sciences, vol. 91, pp. 9141–9145 (Sep. 1994).

Pompliano, D. L., "Steady–State Kinetic Mechanism of Ras Farnesyl:Protein Transferase", Biochemistry, vol. 31, pp. 3800–3807 (1992).

Primary Examiner—Johann Richter
Assistant Examiner—Laura L. Stockton
Attorney, Agent, or Firm—David A. Muthard; Mark R. Daniel

[57] ABSTRACT

The present invention comprises dipeptide analogs that inhibit the farnesylation of Ras. These farnesyl-protein transferase inhibitors are characterized by the inclusion of a cyclic amine in the backbone of the dipeptide. Further contained in this invention are chemotherapeutic compositions containing these farnesyl transferase inhibitors and methods for their production.

18 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093– 1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., *ibid*). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., *ibid;* Casey et al., *ibid;* Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell,* 62:81–88 (1990); Schaber et al., *J. Biol. Chem.,* 265:14701–14704 (1990); Schafer et al., *Science,* 249:1133–1139(1990); Manne et al., *Proc. Natl. Acad. Sci USA,* 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., *ibid,* showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., *ibid;* Reiss et. al., *ibid;* Reiss et al., *PNAS,* 88:732–736 (1991)). Previously described CA$_1$A$_2$X-type FPTase inhibitors contain acyclic amino acids in the second position. Incorporation of proline in the A$_1$ position in such inhibitors has been shown to be the least well tolerated amino acid substitution in that position (Reiss et al., *PNAS* (1991)). Such inhibitors may inhibit while serving as alternate substrates for the Ras farnesyl-transferase enzyme, or may be purely competitive inhibitors (U.S. Pat. No. 5,141,851, University of Texas).

It has also been demonstrated that certain inhibitors of farnesyl-protein transferase selectively block the processing of Ras oncoprotein intracellularly (N. E. Kohl et al., *Science,* 260:1934–1937 (1993) and G. L. James et al., *Science,* 260:1937–1942 (1993)).

Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994)).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et al., *J. Antibiotics* 46:222 (1993)).

It is, therefore, an object of this invention to develop tetrapeptide-based compounds which incorporate a cyclic amino acid in the second position, and which will inhibit farnesyl transferase and the post-translational functionalization of the oncogene Ras protein. It is a further object of this invention to develop chemotherapeutic compositions containing the compounds of this invention and methods for producing the compounds of this invention.

3
SUMMARY OF THE INVENTION

The present invention comprises dipeptide analogs that inhibit the farnesylation of Ras. These compounds differ from those previously described as preferred inhibitors of Ras farnesyl transferase in that, in addition to being dipeptide-like, they incorporate a cyclic amine moiety in the position corresponding to the second amino acid of the dipeptide-like structure. Further contained in this invention are chemotherapeutic compositions containing these farnesyl transferase inhibitors and methods for their production.

The compounds of this invention are illustrated by the formulae:

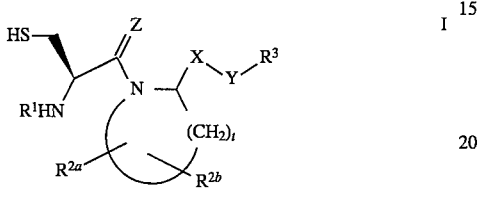
I

DETAILED DESCRIPTION OF THE INVENTION

The compounds of this invention inhibit the farnesylation of Ras. In a first embodiment of this invention, the Ras farnesyl transferase inhibitors are illustrated by the formula I:

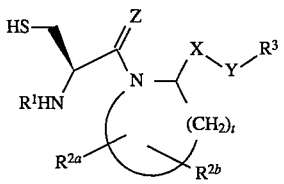
I wherein:
$R^1$ is selected from:
a) hydrogen,
b) $R^5S(O)_2$—, $R^5C(O)$—, $(R^5)_2NC(O)$— or $R^6OC(O)$—, and
c) $C_1$–$C_6$ alkyl unsubstituted or substituted by aryl, heterocyclic, cycloalkyl, alkenyl, alkynyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—;

$R^{2a}$ and $R^{2b}$ are independently selected from:
a) hydrogen,
b) $C_1$–$C_6$ alkyl unsubstituted or substituted by aryl, heterocycle, cycloalkyl, alkenyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—, and
c) aryl, heterocycle, cycloalkyl, alkenyl, $R^5O$—, $R^5S(O)_m$—, $R^5C(O)NR^5$—, CN, $NO_2$, $(R^5)_2N$—$C(NR^5)$—, $R^5C(O)$—, $R^5OC(O)$—, $N_3$, —$N(R^5)_2$, or $R^6OC(O)NR^5$—, $R^3$ is selected from:
a) unsubstituted or substituted aryl,
b) unsubstituted or substituted heterocycle,
c) unsubstituted or substituted cycloalkyl, and
d) $C_1$–$C_6$ alkyl substituted with hydrogen or an unsubstituted or substituted group selected from aryl, heterocycle and cycloalkyl;

X-Y is

4

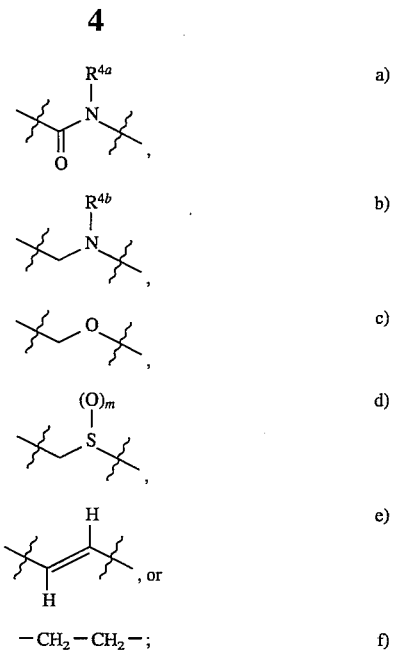

$R^{4a}$ is selected from
a) hydrogen,
b) unsubstituted or substituted aryl,
c) unsubstituted or substituted heterocycle,
d) unsubstituted or substituted cycloalkyl, and
e) $C_1$–$C_6$ alkyl substituted with hydrogen or an unsubstituted or substituted group selected from aryl, heterocycle and cycloalkyl;

$R^{4b}$ is selected from
a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;

$R^5$ is independently selected from hydrogen, $C_1$–$C_6$ alkyl and aryl;
$R^6$ is independently selected from $C_1$–$C_6$ alkyl and aryl;
Z is independently $H_2$ or O;
m is 0, 1 or 2, provided that m is 0 when $R^5$=hydrogen;
n is 0, 1, 2, 3 or 4; and
t is 3, 4 or 5;
or the pharmaceutically acceptable salts thereof.

In a more preferred embodiment of this invention, the Ras farnesyl transferase inhibitors are illustrated by the formula I:

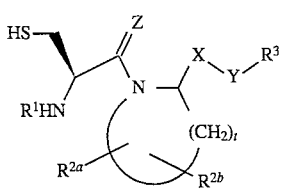

wherein:
R¹ is selected from:
  a) hydrogen,
  b) R⁵S(O)₂—, R⁵C(O)—, (R⁵)₂NC(O)— or R⁶OC(O)—, and
  c) C₁–C₆ alkyl unsubstituted or substituted by aryl, heterocyclic, cycloalkyl, alkenyl, alkynyl, R⁵O—, R⁵S(O)$_m$—, R⁵C(O)NR⁵—, CN, (R⁵)₂N—C(NR⁵)—, R⁵C(O)—, R⁵OC(O)—, N₃, —N(R⁵)₂, or R⁶OC(O)NR⁵—;

R²ᵃ and R²ᵇ are independently selected from:
  a) hydrogen,
  b) C₁–C₆ alkyl unsubstituted or substituted by aryl, heterocycle, cycloalkyl, alkenyl, R⁵O—, R⁵S(O)$_m$—, R⁵C(O)NR⁵—, CN, (R⁵)₂N—C(NR⁵)—, R⁵C(O)—, R⁵OC(O)—, N₃, —N(R⁵)₂, or R⁶OC(O)NR⁵—, and
  c) aryl, heterocycle, cycloalkyl, alkenyl, R⁵O—, R⁵S(O)$_m$—, R⁵C(O)NR⁵—, CN, NO₂, (R⁵)₂N—C(NR⁵)—, R⁵C(O)—, R⁵OC(O)—, N₃, —N(R⁵)₂, or R⁶OC(O)NR⁵—, R³ is selected from:
  a) unsubstituted or substituted aryl,
  b) unsubstituted or substituted heterocycle,
  c) unsubstituted or substituted cycloalkyl, and
  d) C₁–C₆ alkyl substituted with an unsubstituted or substituted group selected from aryl, heterocycle and cycloalkyl;

X-Y is

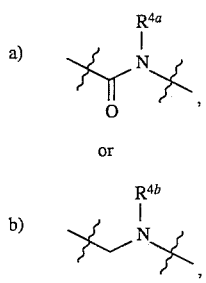

R⁴ᵃ is selected from
  a) hydrogen,
  b) unsubstituted or substituted aryl,
  c) unsubstituted or substituted heterocycle,
  d) unsubstituted or substituted cycloalkyl, and
  e) C₁–C₆ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R⁴ᵇ is selected from
  a) hydrogen,
  b) unsubstituted or substituted aryl,
  c) unsubstituted or substituted heterocycle,
  d) unsubstituted or substituted cycloalkyl,
  e) C₁–C₆ alkyl substituted with hydrogen or an unsubstituted or substituted group selected from aryl, heterocycle and cycloalkyl,
  f) a carbonyl group which is bonded to an unsubstituted or substituted group selected from aryl, heterocycle, cycloalkyl and C₁–C₆ alkyl substituted with hydrogen or an unsubstituted or substituted group selected from aryl, heterocycle and cycloalkyl, and
  g) a sulfonyl group which is bonded to an unsubstituted or substituted group selected from aryl, heterocycle, cycloalkyl and C₁–C₆ alkyl substituted with hydrogen or an unsubstituted or substituted group selected from aryl, heterocycle and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

R⁵ is independently selected from hydrogen, C₁–C₆ alkyl and aryl;
R⁶ is independently selected from C₁–C₆ alkyl and aryl;
Z is independently H₂ or O;
m is 0, 1 or 2, provided that m is 0 when R⁵=hydrogen;
n is 0, 1, 2, 3 or 4; and
t is 3, 4 or 5;
or the pharmaceutically acceptable salts thereof.

The preferred compounds of this invention are as follows:
N-[2(R)-Amino-3-mercaptopropyl]-L-proline-2,3-dichlorobenzylamide
N-[2(R)-Amino-3-mercaptopropyl]-L,proline-1-naphthylmethyl amide
N-[2(R)-Amino-3-mercaptopropyl]-L-pipecolyl-2,3-dichlorobenzamide
N-[2(R)-Amino-3-mercaptopropyl]-L-3-trans-ethylproline-2,3-dichlorobenzamide
N-[2(R)-Amino-3-mercaptopropyl]-D-3-trans-ethylproline-2,3-dichlorobenzamide
N-[2(R)-Amino-3-mercaptopropyl]-L-3-cis-ethylproline-2,3-dichlorobenzamide
N-[2(R)-Amino-3-mercaptopropyl]-D-3-cis-ethylproline-2,3-dichlorobenzamide
N-[2(R)-Amino-3-mercaptopropyl]-L-3-trans-ethylproline-1-naphthylmethyl amide
N-[2(R)-Amino-3-mercaptopropyl]-D-3-trans-ethylproline-1-naphthylmethyl amide
N-[2(R)-Amino-3-mercaptopropyl]-L-proline-2,3-dimethylphenyl amide
N-[2(R)-Amino-3-mercaptopropyl]-L-3-trans-ethylproline-2,3-dimethylphenyl amide
N-[2(R)-Amino-3-mercaptopropyl]-D-3-trans-ethylproline-2,3-dimethylphenyl amide
or the pharmaceutically acceptable salts thereof.

The most preferred compounds of the invention are:

N-[2(R)-Amino-3-mercaptopropyl]-L-3-trans-ethylproline-2,3-dichlorobenzamide

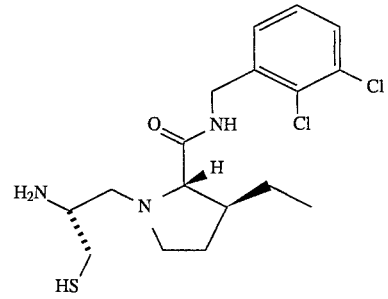

N-[2(R)-Amino-3-mercaptopropyl]-L-3-cis-ethylproline-2,3-dichlorobenzamide

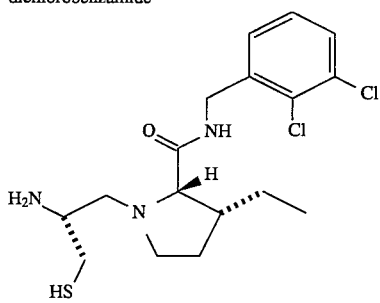

N-[2(R)-Amino-3-mercaptopropyl]-L-3-trans-ethylproline-1-naphthylmethyl amide

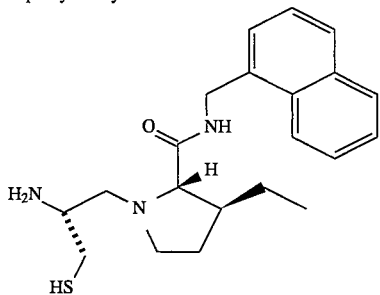

N-[2(R)-Amino-3-mercaptopropyl]-L-3-trans-ethylproline-2,3-dimethylphenyl amide

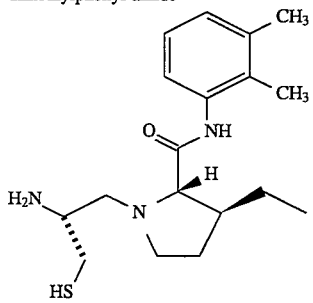

or the pharmaceutically acceptable salts thereof.

In the present invention, the amino acids which are disclosed are identified both by conventional 3 letter and single letter abbreviations as indicated below:

| Alanine | Ala | A |
|---|---|---|
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydro-benzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, NH$_2$, N(C$_1$–C$_6$ alkyl)$_2$, NO$_2$, (C$_1$–C$_6$ alkyl)O—, —OH, (C$_1$–C$_6$ alkyl)S(O)$_m$—, (C$_1$–C$_6$ alkyl)C(O)NH—, CN, H$_2$N—C(NH)—, (C$_1$–C$_6$ alkyl)C(O)—, (C$_1$–C$_6$ alkyl)OC(O)—, N$_3$, (C$_1$–C$_6$ alkyl)OC(O)NH— and C$_1$–C$_{20}$ alkyl.

The following structure:

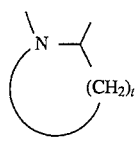

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

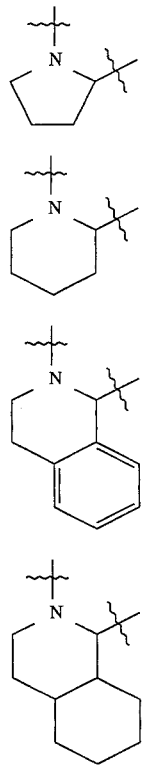

It is also understood that substitution on the cyclic amine moiety by $R^{2a}$ and $R^{2b}$ may be on different carbon atoms or on the same carbon atom.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^5$, etc.) at a particular location in a molecule be independent of its definitions elsewhere in that molecule. Thus, —$N(R^5)_2$ represents —NHH, —$NHCH_3$, —$NHC_2H_5$, etc. It is understood that substituents and substitution patters on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "*Solid Phase Peptide Synthesis*", Second Edition, Pierce Chemical Company, 1984. The teachings of these works are hereby incorporated by reference.

Abbreviations used in the description of the chemistry and in the Examples that follow are:
$Ac_2O$ Acetic anhydride;
Boc t-Butoxycarbonyl;
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimidehydrochloride;
HOBT 1-Hydroxybenzotriazole hydrate;
$Et_3N$ Triethylamine;
EtOAc Ethyl acetate;
FAB Fast atom bombardment;
HOOBT 3-Hydroxy- 1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide;
Py Pyridine;
TFA Trifluoroacetic acid;
THF Tetrahydrofuran.

Compounds of this invention are prepared by employing the reactions shown in the following Reaction Schemes A–F, in addition to other standard manipulations such as ester hydrolysis, cleavage of protecting groups, etc., as may be known in the literature or exemplified in the experimental procedures.

REACTION SCHEME A

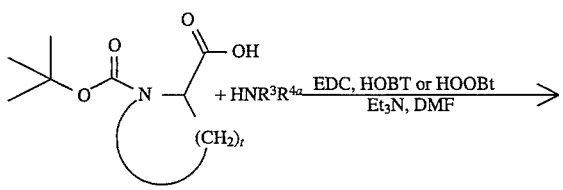

-continued
REACTION SCHEME A

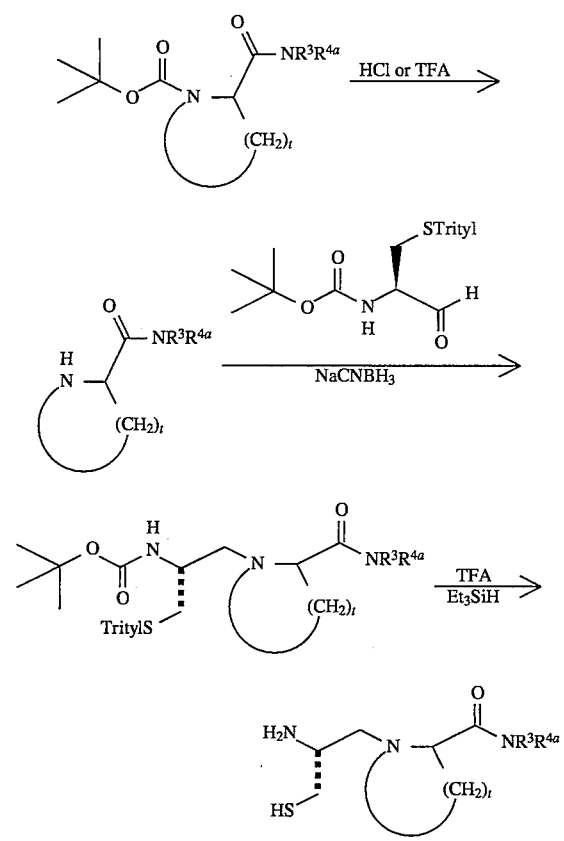

REACTION SCHEME B

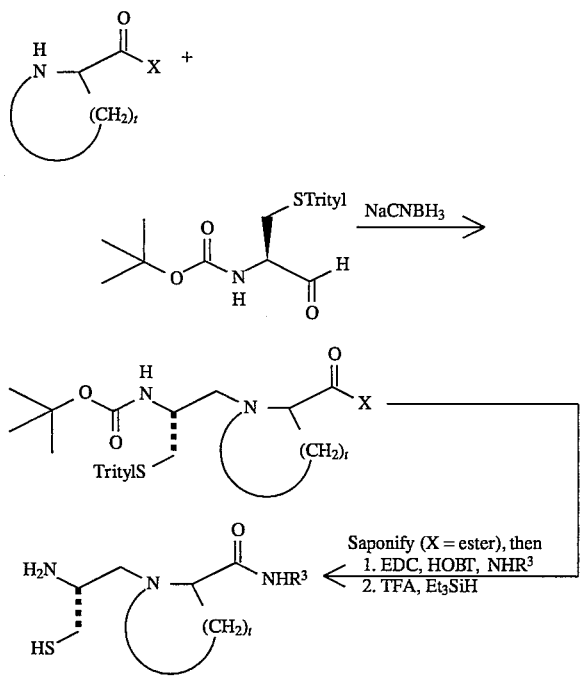

where X is OH or an ester.

In Reaction Scheme A, coupling of a protected amino acid with the appropriate amine is accomplished using standard peptide coupling conditions. The resulting amino acid amide is deprotected and the primary amine is reductively alkylated with a protected cysteine-derived aldehyde using sodium cyanoborohydride or sodium triacetoxyborohydride. Finally, removal of the protecting groups provides the compounds of interest.

In Reaction Scheme B, a different strategy for synthesis is described. Reductive alkylation of an amino acid provides a protected dipeptide isostere. The same versatile intermediate can be obtained by reductive alkylation of an amino acid ester followed by saponification. This intermediate can be coupled with any of a number of amines using standard peptide coupling conditions. Deprotection provides the active farnesyl transferase inhibitors.

The choice of protecting groups shown in the scheme is not unique and the chemical reactions employed in these syntheses are compatible with other amine and sulfur protecting groups commonly used in peptide synthesis.

Certain compounds of this invention wherein X-Y is an ethenylene or ethylene unit are prepared by employing the reaction sequences shown in Reaction Schemes C and D. Reaction Scheme C outlines the preparation of the alkene isosteres utilizing standard manipulations such as Wittig reaction, peptide coupling reaction, reductive alkylation, etc., as may be known in the literature or exemplified in the Experimental Procedure. For simplicity, substituents $R^{2a}$ and $R^{2b}$ on the cyclic amine moiety are not shown. It is, however, understood that the reactions illustrated are also applicable to appropriately substituted cyclic amine compounds. In Step B of Scheme C, the cysteinyl amino terminus sidechain, designated $R^x$ is incorporated using coupling reaction A and proR$^x$COOH; or the alkylation reaction C using proR$^x$CHO and a reducing agent. The $R^x$ sidechain is exposed by deprotection of the sulfur moiety.

The alkane analogs are prepared in a similar manner by including an additional catalytic hydrogenation step as outlined in Reaction Scheme D.

REACTION SCHEME C

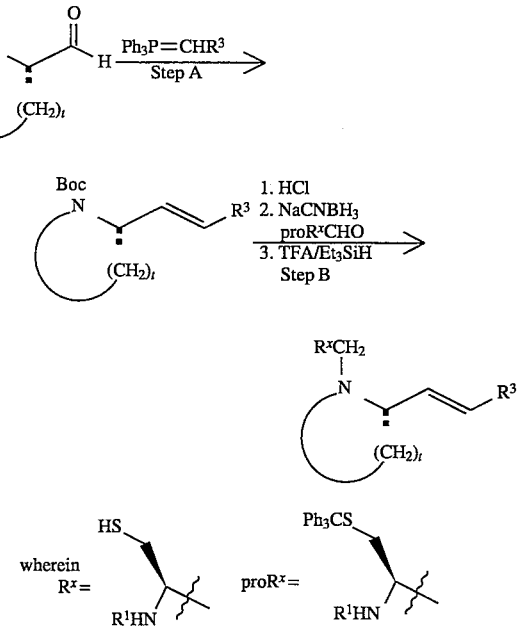

-continued
REACTION SCHEME C or

Alternate Step B

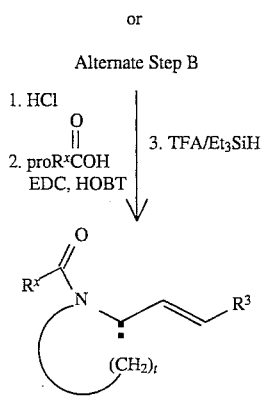

REACTION SCHEME D

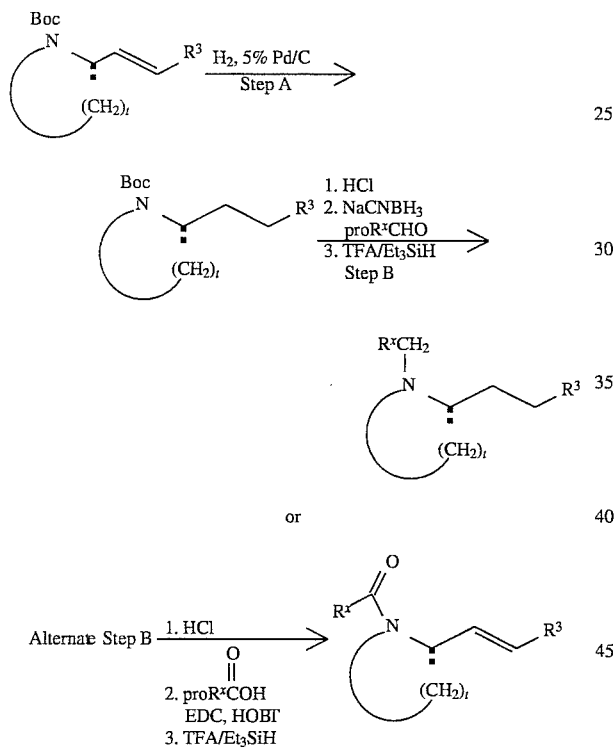

The oxa isostere compounds of this invention are prepared according to the routes outlined in Schemes E and F. Referring to Scheme E, an aminoalcohol 1 is persilylated with trimethylsilyl chloride and then selectively desilylated with limited methanol to yield amine 2. The nitrogen of the amine 2 is then protected and the alcohol unblocked with excess aqueous methanol to provide 3. Alkylation of 3 with $R^3X^L$, where $X^L$ is a leaving group such as $Br^-$, $I^-$ or $Cl^-$ in the presence of a suitable base, preferably NaH, affords 4. Deprotection of alkylated compound 4 provides 5, which undergoes reductive alkylation in the presence of an aldehyde proR$^x$CHO (6) and a reducing agent (e.g., sodium cyanoborohydride); or acylation in the presence of proR$^x$-COOH (7) and a peptide coupling reagent affording, after deprotection of the sulfhydryl moiety, the products 8 and 9.

An alternative method for the preparation of the prolyl oxa isostere (compounds 8 and 9) is illustrated in Scheme F. Referring to Scheme F, the aminoalcohol 1 is protected with trifluoroacetic anhydride and the blocked compound 10 treated with diphenyl disulfide in the presence of tributylphosphine to provide the thioether 11. Chlorination of compound 11 provides compound 12 which can be reacted with a variety of alcohols, $R^3$OH, in the presence of silver perchlorate and tin (II) chloride, to afford the mixed acetal 4. Removal of the phenylmercapto moiety with Raney nickel followed by deprotection of alkylated compound 14 provides the free amine intermediate, which undergoes reductive alkylation in the presence of an aldehyde proR$^x$-CHO (6) and a reducing agent (e.g., sodium cyanoborohydride); or acylation in the presence of proR$^x$COOH (7) and a peptide coupling reagent affording, after deprotection of the sulfhydryl moiety, the products 8 and 9.

Yet another alternative method for the preparation of the prolyl oxa isostere (compounds 8 and 9) is described in the literature [Ruth E. TenBrink, *J. Org. Chem.*, 52:418–422 (1987)].

SCHEME E

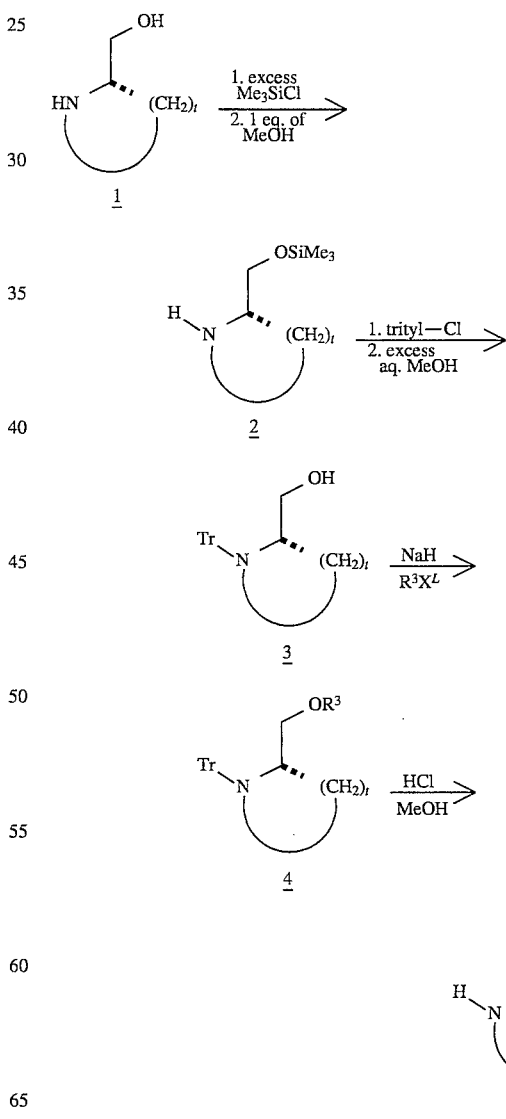

-continued
SCHEME E

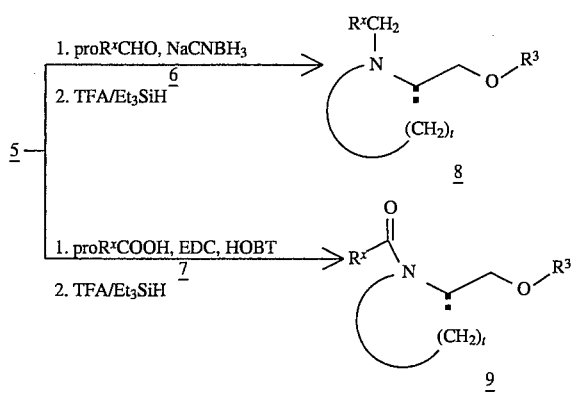

The thia, oxothia and dioxothia isostere compounds of this invention are prepared in accordance to the route depicted in Scheme G. Aminoalcohol 1 is derivatized with trifluoroacetic anhydride to give 9. Mesylation of 9 provided 15 which is reacted with an appropriate mercaptan to provide 16. The sulfide 16 is readily oxidized to either the sulfoxide or the sulfone by the use of MCPBA (m-chloroperoxybenzoic acid). Removal of the triflate group in 16 with aqueous HCl the amine 17. This amine hydrochloride 17 undergoes reductive alkylation in the presence of an aldehyde R$^x$CHO (6) and a reducing agent (e.g., sodium cyanoborohydride); or acylation in the presence of R$^x$COOH (7) and a peptide coupling reagent to afford, after deprotection of the sulfhydryl moiety, the products 18 and 19.

SCHEME F

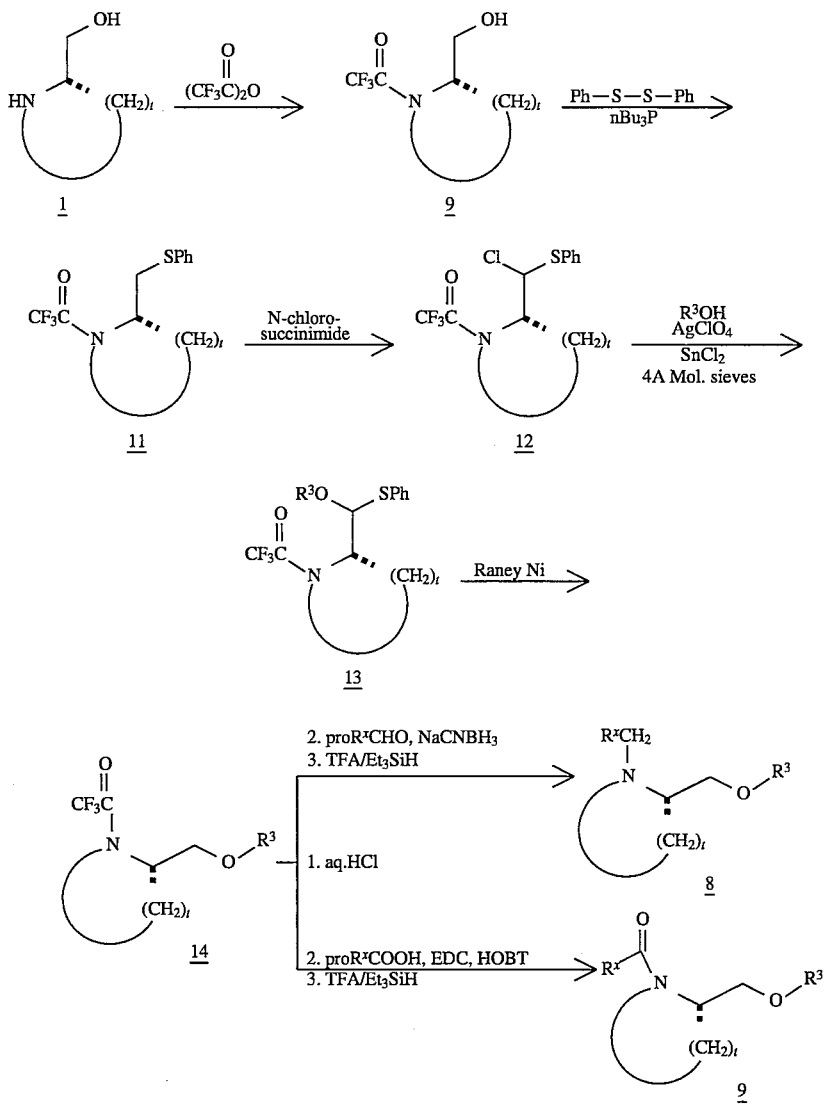

SCHEME G

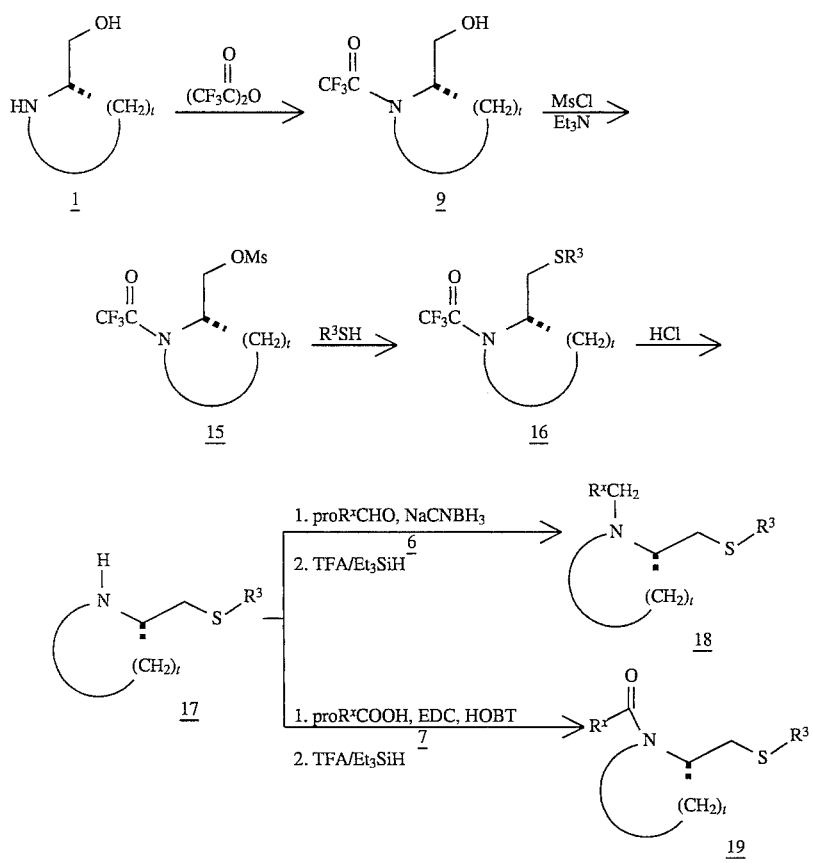

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the an that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

N-[2(R)-Amino-3-mercaptopropyl-L-proline-2,3-dichlorobenzamide

Step A: 2(R)-t-Butoxycarbonylamino-3-triphenylmethylmercaptopropanal

The aldehyde was synthesized by the method described in U.S. Pat. No. 5,238,922 (Col. 10).

$^1$H NMR (CDCl$_3$) δ 9.64 (s, 1H), 7.42 (m, 6H), 7.28 (m, 9H), 2.45 (m, 2H), 2.38 (m, 2H).

Step B: [2(R)-(t-butyloxycarbonyl)amino-3-triphenylmethylmercaptopropyl] -L-proline methyl ester Proline methyl ester hydrochloride (0.166 g, 1 mmol) and 2-t-butoxycarbonylamino-3-triphenylmethylmercaptopropanal (0.538 g, 1.2 mmol) were dissolved in MeOH (8 mL), treated with 3A molecular sieves (0.16 g), KOAc (0.98 g, 1 mmol) and solid sodium cyanoborohydride (0.094 g, 1.5 mmol), then stirred at ambient temperature for 24 hr. The reaction mixture was filtered, concentrated, then the residue was partitioned between EtOAc and aq satd NaHCO$_3$ soln.

The organic layer was washed with brine, dried (Na$_2$SO$_4$), filtered and concentrated to provide the title compound after chromatography (SiO$_2$) with EtOAc: hexane, 1:5. $^1$H NMR (CDCl$_3$) δ 7.2–7.4 (m, 15H), 4.75–4.85 (m, 1H), 3.67 (s, 3H), 3.6–3.75 (m, 1H), 3.18–3.28 (m, 1H), 2.9–3.0 (m, 1H), 2.35–2.65 (m, 4H), 1.75–2.0 (m, 4H), 1.45 (s, 9H), 1.2–1.4 (m, 1H).

Step C: [2(R)-(t-butoxycarbonyl)amino-3-triphenylmethylmercaptopropyl] -L-proline

[2(R)-(t-butyloxycarbonyl)amino-3-triphenylmethylmercaptopropyl] -L-proline methyl ester (0.325 g, 0.58 mmol) was dissolved in MeOH (12 mL) and 1N NaOH solution (2.3 mL, 2.3 mmol) with stirring at ambient temperature. After 24 hrs, the reaction mixture was concentrated to remove MeOH, then dissolved in H$_2$O, neutralized with 1N HCl (2.3 mL, 2.3 mmol), and extracted with EtOAc (3×10 mL). The organics were combined, washed with brine and dried (Na$_2$SO$_4$). Filtration and concentration to dryness provided the title compound. $^1$H NMR (CD$_3$OD) δ 7.2–7.5 (m, 15H), 3.7–3.85 (m, 1H), 3.5–3.7 (m, 2H), 2.9–3.15 (m, 3H), 2.2–2.6 (m, 3H), 1.8–2.2 (m, 3H), 1.48 (s, 9H).

Step D: N-[2(R)-t-Butoxycarbonylamino-3-triphenylmethylmercaptopropyl] -L-proline-2,3-dichlorobenzamide

[2(R)-(t-butoxycarbonyl)amino-3-triphenylmethylmercaptopropyl] -L-proline (0.08 g, 0.153 mmol), 1-(3-dimethylaminopropyl)- 3-ethylcarbodiimide (EDC) (0.035 g, 0.184 mmol), and 1-hydroxybenzotriazole hydrate (HOBT) (0.025 g, 0.184 mmol) were dissolved in DMF (2 mL), treated with 2,3-dichlorobenzylamine (0.025 mL, 0.184 mmol), and brought to pH 7 with Et$_3$N (0.026 mL, 0.184 mmol). After stirring at ambient temperature for 18 h the mixture was concentrated to dryness, and the residue was partitioned between EtOAc and H$_2$O, the organic layer separated, washed with aq satd NaHCO$_3$, brine, and dried (Na$_2$SO$_4$). Filtration and concentration provided the title compound. $^1$H NMR (CD$_3$OD) δ 7.1–7.5 (m, 18H), 4.53 (d, 1H, J=8 Hz), 4.26 (d, 1H, J=8 Hz), 3.64–3.76 (m, 1H), 2.96–3.14 (m, 2H), 2.52– 2.66 (m, 1H), 2.1–2.5 (m, 5H), 1.6–1.9 (m, 3H), 1.45 (s, 9H).

Step E: N-[2(R)-Amino-3-mercaptopropyl]-L-proline- 2,3-dichlorobenzamide

N-[2(R)-t-Butoxycarbonylamino-3-triphenylmethylmercaptopropyl] -L-proline-2,3-dichlorobenzamide (0.097 g, 0.14 mmol) was dissolved in CH$_2$Cl$_2$ (3 mL), CF$_3$CO$_2$H (1 mL) at ambient temperature, treated with triethylsilane (0.088 mL, 0.55 mmol) and stirred for 1 h. The reaction mixture was triturated with 0.1% TFA in H$_2$O, filtered, concentrated and chromatographed by RP-HPLC and lyophilized. The residue was dissolved in MeOH (1 mL), treated with concd HCl, concentrated and triturated with Et$_2$O to provide the title compound as the his hydrochloride salt. $^1$H NMR (CD$_3$OD) δ 7.50 (d, 1H, J=6 Hz), 7.27–7.4 (m, 2H), 4.60 (ABq, 2H), 4.25–4.7 (m, 1H), 3.3– 3.9 (m, 5H), 2.99 (d, 2H, J=5 Hz), 2.5–2.7 (m, 1H), 2.0–2.3 (m, 3H).

Anal. calcd for C$_{15}$H$_{21}$N$_3$OSCl$_2$·2.75 HCl: C, 38.97; H, 5.18, N, 9.09; found C, 38.63; H, 5.21; N, 8.86.

Using the methods described in Example 1, but a different cyclic amino acid in Step B or a different amine in Step D the following compound were prepared:

N-[2(R)-Amino-3-mercaptopropyl]-L-proline-1-naphthylmethyl amide

Anal. calcd for C$_{19}$H$_{25}$N$_3$OS·2.1 CF$_3$CO$_2$H·0.1 H$_2$O: C, 47.66; H, 4.71; N, 7.19; found C, 47.68; H, 4.57; N, 7.02.

N-[2(R)-Amino-3-mercaptopropyl]-L-pipecolyl-2,3-dichlorobenzamide

Anal. calcd for C$_{16}$H$_{23}$N$_3$OSCl$_2$·2.5 CF$_3$CO$_2$H: C, 38.13; H, 3.89, N, 6.35; found C, 38.20; H, 3.65; N, 6.68.

N-[2(R)-Amino-3-mercaptopropyl]-L-3-trans-ethylproline-2,3-dichlorobenzamide
MS (M+1)=390.
N-[2(R)-Amino-3-mercaptopropyl]-D-3-trans-ethylproline-2,3-dichlorobenzamide
Anal. calcd for $C_{17}H_{25}N_3OSCl_2 \cdot 2.75\ CF_3CO_2H$: C, 38.39; H, 3.97; N, 5.97; found C, 38.39; H, 3.97; N, 6.27.
N-[2(R)-Amino-3-mercaptopropyl]-L-3-cis-ethylproline-2,3-dichlorobenzamide
Anal. calcd for $C_{17}H_{25}N_3OSCl_2 \cdot 2.75\ CF_3CO_2H$: C, 38.39; H, 3.97; N, 5.97; found C, 38.51; H, 4.18; N, 6.28.
N-[2(R)-Amino-3-mercaptopropyl]-D-3-cis-ethylproline-2,3-dichlorobenzamide
Anal. calcd for $C_{17}H_{25}N_3OSCl_2 \cdot 2.5\ CF_3CO_2H$: C, 39.12; H, 4.10; N, 6.22; found C, 39.03; H, 4.22; N, 6.47.
N-[2(R)-Amino-3-mercaptopropyl]-L-3-trans-ethylproline-1-naphthylmethyl amide
Anal. calcd for $C_{21}H_{29}N_3OS \cdot 2.25\ CF_3CO_2H$: C, 48.76; H, 5.02; N, 6.69; found C, 48.63; H, 5.10; N, 6.89.
N-[2(R)-Amino-3-mercaptopropyl]-D-3-trans-ethylproline-1-naphthylmethyl amide
Anal. calcd for $C_{21}H_{29}N_3OS \cdot 85\ CF_3CO_2H$: C, 50.93; H, 5.34; N, 7.21; found C, 50.88; H, 5.43; N, 7.41.

EXAMPLE 2

N-[2(R)-Amino-3-mercaptopropyl]-L-proline-2,3-dimethylphenyl amide
Step A: N-[2(R)-t-butoxycarbonylamino-3-triphenyl methylmercaptopropyl]-L-proline-2,3-dimethylphenyl amide To a solution of 2,3-dimethylaniline (0.05 mL, 0.41 mmol) and diisopropylethylamine (0.12 mL, 0.69 mmol) in $CH_2Cl_2$ (4 mL) was added N-[2(R)-t-butoxycarbonylamino-3-triphenylmethyl mercaptopropyl]-L-proline (Example 1, Step C) (0.18 g, 0.34 mmol) followed by bis(2-oxo-3-oxazolidinyl)phosphinic chloride (BOP-Cl) (0.175 g, 0.69 mmol) with stirring under argon at ambient temperature. After stirring for 20 h the solution was concentrated to dryness, and taken up in $H_2O$ (30 mL) and extracted with EtOAc (3×20 mL). The organics were combined, washed with aq citric acid soln, aq satd $NaHCO_3$ soln, brine and dried ($Na_2SO_4$). Filtration and concentration followed by chromatography ($SiO_2$) ($CH_2Cl_2$: MeOH, 98:2)) provided the title compound. $^1H$ NMR ($CD_3OD$) δ 7.0–7.42 (m, 18H), 3.78–3.88 (m, 1H), 3.06–3.19 (m, 2H), 2.14–2.7 (m, 6H), 2.26 (s, 3H), 1.93 (s, 3H), 1.66–1.99 (m, 3H), 1.41 (s, 9H).
Step B: N-[2(R)-Amino-3-mercaptopropyl]-L-proline-2,3-dimethylphenylamide N-[2(R)-t-butoxycarbonylamino-3-triphenylmethylmercapto-propyl]-L-proline-2,3-dimethylphenyl amide (0.124 g, 0.19 mmol) was dissolved in $CH_2Cl_2$ (3 mL) and $CF_3CO_2H$ (1 mL) at ambient temperature, treated with triethylsilane (0.121 mL, 0.76 mmol) and stirred for 2 h. The reaction mixture was concentrated, triturated with 0.1% aq TFA soln, the solid precipitate filtered off, and the filtrate lyophilized to provide the title compound. $^1H$ NMR ($CD_3OD$) δ 7.10 (s, 3H), 3.55–3.68 (m, 1H), 3.32–3.45 (m, 2H), 2.75–3.19 (m, 5H), 2.5–2.65 (m, 1H), 2.31 (s, 3H), 2.15 (s, 3H), 1.9–2.15 (m, 3H).
Anal. calcd for $C_{16}H_{25}N_3OS \cdot 2.7\ CF_3CO_2H$: C, 41.77; H, 4.54; N, 6.83; found: C, 41.70; H, 4.81; N, 7.17.
Using the methods described in Example 2 the following compounds were prepared:
N-[2(R)-Amino-3-mercaptopropyl]-L-3-trans-ethylproline-2,3-dimethylphenyl amide
Anal. calcd for $C_{18}H_{29}N_3OS \cdot 3\ CF_3CO_2H$: C, 42.54; H, 4.76; N, 6.20; found C, 42.16; H, 5.06; N, 6.64.

N-[2(R)-Amino-3-mercaptopropyl]-D-3-trans-ethylproline-2,3-dimethylphenyl amide
Anal. calcd for $C_{18}H_{29}N_3OS \cdot 2.5\ CF_3CO_2H$: C, 44.51; H, 5.12, N, 6.77; found C, 44.80; H, 5.19; N, 6.83.

EXAMPLE 3

In vitro inhibition of ras farnesyl transferase
Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989). Bovine FPTase was assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3H$]-farnesyl diphosphate ([$^3H$]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and tinge; less than 10% of the [$^3H$]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM $ZnCl_2$ and 100 nm Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have $IC_{50}$ of <10 μM.

EXAMPLE 4

In vivo ras farnesylation assay
The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}S$]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 5

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyl-transferase having the formula I:

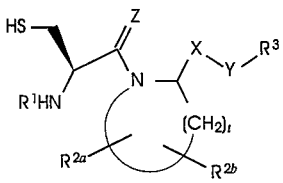

wherein:

$R^1$ is selected from:
a) hydrogen,
b) $R^5S(O)_2-$, $R^5C(O)-$, $(R^5)2NC(O)-$ or $R^6OC(O)-$, and
c) $C_1-C_6$ alkyl unsubstituted or substituted by aryl, heterocyclic, cycloalkyl, alkenyl, alkynyl, $R^5O-$, $R^5S(O)_m-$, $R^5C(O)NR^5-$, CN, $(R^5)_2N-C(NR^5)-$, $R^5C(O)-$, $R^5OC(O)-$, $N_3$, $-N(R^5)_2$, or $R^6OC(O)NR^5-$;

$R^{2a}$ and $R^{2b}$ are independently selected from:
a) hydrogen,
b) $C_1-C_6$ alkyl unsubstituted or substituted by aryl, heterocycle, cycloalkyl, alkenyl, $R^5O-$, $R^5S(O)_m-$, $R^5C(O)NR^5-$, CN, $(R^5)_2N-C(NR^5)-$, $R^5C(O)-$, $R^5OC(O)-$, $N_3$, $-N(R^5)_2$, or $R^6OC(O)NR^5-$, and
c) aryl, heterocycle, cycloalkyl, alkenyl, $R^5O-$, $R^5S(O)_m-$, $R^5C(O)NR^5-$, CN, $NO_2$, $(R^5)_2N-C(NR^5)-$, $R^5C(O)-$, $R^5OC(O)-$, $N_3$, $-N(R^5)_2$, or $R^6OC(O)NR^5-$, $R^3$ is selected from:
a) unsubstituted or substituted aryl,
b) unsubstituted or substituted heterocycle,
c) unsubstituted or substituted cycloalkyl, and
d) $C_1-C_6$ alkyl substituted with hydrogen or an unsubstituted or substituted group selected from aryl, heterocycle and cycloalkyl;

X-Y is

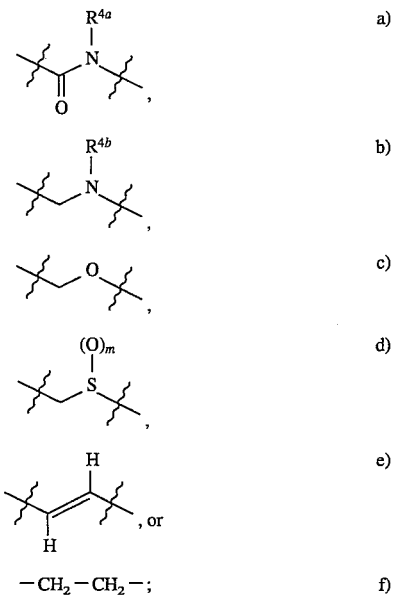

$R^{4a}$ is selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;

$R^{4b}$ is selected from
a) hydrogen,
b) unsubstituted or substituted aryl,
c) unsubstituted or substituted heterocycle,
d) unsubstituted or substituted cycloalkyl,
e) $C_1-C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1-C_6$ alkyl substituted with hydrogen or an unsubstituted or substituted group selected from aryl, heterocycle and cycloalkyl;

$R^5$ is independently selected from hydrogen, $C_1-C_6$ alkyl and aryl;

$R^6$ is independently selected from $C_1-C_6$ alkyl and aryl;

Z is $H_2$;

m is 0, 1 or 2, provided that m is 0 when $R^5$=hydrogen;

n is 0, 1, 2, 3 or 4; and t is 3;

or a pharmaceutically acceptable salt thereof.

2. The compound according to claim 1 having a structure of the formula I:

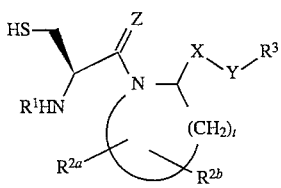

wherein:
$R^1$ is selected from:
a) hydrogen,
b) $R^5S(O)_2$—, $R^5C(O)$—, $(R^5)_2NC(O)$— or $R^6OC(O)$—, and
c) $C_1$–$C_6$ alkyl unsubstituted or substituted by aryl, heterocyclic, cycloalkyl, alkenyl, alkynyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—;

$R^{2a}$ and $R^{2b}$ are independently selected from:
a) hydrogen,
b) $C_1$–$C_6$ alkyl unsubstituted or substituted by aryl, heterocycle, cycloalkyl, alkenyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—, and
c) aryl, heterocycle, cycloalkyl, alkenyl, $R^5O$—, $R^5S(O)_m$—, $R^5C(O)NR^5$—, CN, $NO_2$, $(R^5)_2N$—$C(NR^5)$—, $R^5C(O)$—, $R^5OC(O)$—, $N_3$, —$N(R^5)_2$, or $R^6OC(O)NR^5$—, $R^3$ is selected from:
a) unsubstituted or substituted aryl,
b) unsubstituted or substituted heterocycle,
c) unsubstituted or substituted cycloalkyl, and
d) $C_1$–$C_6$ alkyl substituted with an unsubstituted or substituted group selected from aryl, heterocycle and cycloalkyl;

X-Y is

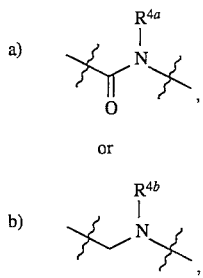

$R^{4a}$ is selected from
a) hydrogen,
b) unsubstituted or substituted aryl,
c) unsubstituted or substituted heterocycle,
d) unsubstituted or substituted cycloalkyl, and
e) $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{4b}$ is selected from
a) hydrogen,
b) unsubstituted or substituted aryl,
c) unsubstituted or substituted heterocycle,
d) unsubstituted or substituted cycloalkyl,
e) $C_1$–$C_6$ alkyl substituted with hydrogen or an unsubstituted or substituted group selected from aryl, heterocycle and cycloalkyl,
f) a carbonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl, and
g) a sulfonyl group which is bonded to an unsubstituted or substituted group selected from aryl, heterocycle, cycloalkyl and $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^5$ is independently selected from hydrogen, $C_1$–$C_6$ alkyl and aryl;
$R^6$ is independently selected from $C_1$–$C_6$ alkyl and aryl;
Z is $H_2$;
m is 0, 1 or 2, provided that m is 0 when $R^5$=hydrogen;
n is 0, 1, 2, 3 or 4; and
t is 3;
or a pharmaceutically acceptable salt thereof.

3. The compound according to claim 1 which inhibits Ras farnesyl-transferase having the formula I:

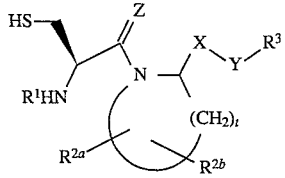

wherein:
$R^1$ is selected from:
a) hydrogen,
b) $R^5S(O)_2$—, $R^5C(O)$—, $(R^5)_2NC(O)$— or $R^6OC(O)$—, and
c) $C_1$–$C_6$ alkyl unsubstituted or substituted by aryl, cycloalkyl, alkenyl, alkynyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—;

$R^{2a}$ and $R^{2b}$ are independently selected from:
a) hydrogen,
b) $C_1$–$C_6$ alkyl unsubstituted or substituted by aryl, cycloalkyl, alkenyl, $R^5O$—, $R^5S(O)_m$—, $R^5C(O)NR^5$—, CN, $(R^5)_2N$—$C(NR^5)$—, $R^5C(O)$—, $R^5OC(O)$—, $N_3$, —$N(R^5)_2$, or $R^6OC(O)NR^5$—, and
c) aryl, cycloalkyl, alkenyl, $R^5O$—, $R^5S(O)_m$—, $R^5C(O)NR^5$—, CN, $NO_2$, $(R^5)_2N$—$C(NR^5)$—, $R^5C(O)$—, $R^5OC(O)$—, $N_3$, —$N(R^5)_2$, or $R^6OC(O)NR^5$—, $R^3$ is selected from:
a) unsubstituted or substituted aryl,
b) unsubstituted or substituted cycloalkyl, and
c) $C_1$–$C_6$ alkyl substituted with an unsubstituted or substituted group selected from aryl and cycloalkyl;

X-Y is

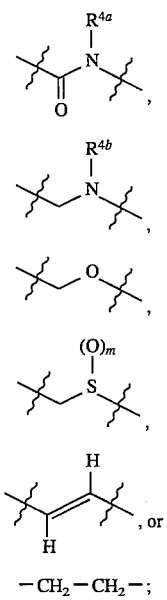

a)

b)

c)

d)

e) , or f) $-CH_2-CH_2-$;

$R^{4a}$ is selected from
a) hydrogen,
b) unsubstituted or substituted aryl,
c) unsubstituted or substituted cycloalkyl, and
d) $C_1-C_6$ alkyl substituted with hydrogen or an unsubstituted or substituted group selected from aryl and cycloalkyl;

$R^{4b}$ is selected from
a) hydrogen,
b) unsubstituted or substituted aryl,
c) unsubstituted or substituted cycloalkyl,
d) $C_1-C_6$ alkyl substituted with hydrogen or an unsubstituted or substituted group selected from aryl and cycloalkyl,
e) a carbonyl group which is bonded to an unsubstituted or substituted group selected from aryl, cycloalkyl and $C_1-C_6$ alkyl substituted with hydrogen or an unsubstituted or substituted group selected from aryl and cycloalkyl, and
f) a sulfonyl group which is bonded to an unsubstituted or substituted group selected from aryl, cycloalkyl and $C_1-C_6$ alkyl substituted with hydrogen or an unsubstituted or substituted group selected from aryl and cycloalkyl;

$R^5$ is independently selected from hydrogen, $C_1-C_6$ alkyl and aryl;
$R^6$ is independently selected from $C_1-C_6$ alkyl and aryl;
Z is $H_2$;
m is 0, 1 or 2, provided that m is 0 when $R^5$=hydrogen;
n is 0, 1, 2, 3 or 4; and
t is 3;
or a pharmaceutically acceptable salt thereof.

4. The compound according to claim 3 having a structure of the formula I:

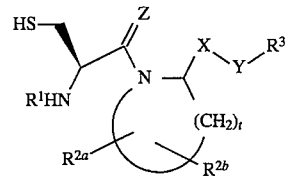

wherein:
$R^1$ is selected from:
a) hydrogen,
b) $R^5S(O)_2-$, $R^5C(O)-$, $(R^5)_2NC(O)-$ or $R^6OC(O)-$, and
c) $C_1-C_6$ alkyl unsubstituted or substituted by aryl, cycloalkyl, alkenyl, alkynyl, $R^5O-$, $R^5S(O)_m-$, $R^5C(O)NR^5-$, CN, $(R^5)_2N-C(NR^5)-$, $R^5C(O)-$, $R^5OC(O)-$, $N_3$, $-N(R^5)_2$, or $R^6OC(O)NR^5-$;

$R^{2a}$ and $R^{2b}$ are independently selected from:
a) hydrogen,
b) $C_1-C_6$ alkyl unsubstituted or substituted by aryl, cycloalkyl, alkenyl, $R^5O-$, $R^5S(O)_m-$, $R^5C(O)NR^5-$, CN, $(R^5)_2N-C(NR^5)-$, $R^5C(O)-$, $R^5OC(O)-$, $N_3$, $-N(R^5)_2$, or $R^6OC(O)NR^5-$, and
c) aryl, cycloalkyl, alkenyl, $R^5O-$, $R^5S(O)_m-$, $R^5C(O)NR^5-$, CN, $NO_2$, $(R^5)_2N-C(NR^5)-$, $R^5C(O)-$, $R^5OC(O)-$, $N_3$, $-N(R^5)_2$, or $R^6OC(O)NR^5-$, $R^3$ is selected from:
a) unsubstituted or substituted aryl,
b) unsubstituted or substituted cycloalkyl, and
c) $C_1-C_6$ alkyl substituted with an unsubstituted or substituted group selected from aryl and cycloakyl;

X-Y is a) 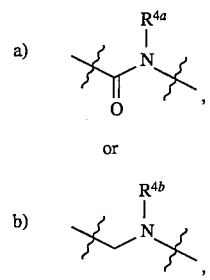

or b)

$R^{4a}$ is selected from
a) hydrogen,
b) unsubstituted or substituted aryl,
c) unsubstituted or substituted cycloalkyl, and
d) $C_1-C_6$ alkyl substituted with hydrogen or an unsubstituted or substituted group selected from aryl and cycloalkyl;

$R^{4b}$ is selected from
a) hydrogen,
b) unsubstituted or substituted aryl,
c) unsubstituted or substituted cycloalkyl,
d) $C_1-C_6$ alkyl substituted with hydrogen or an unsubstituted or substituted group selected from aryl and cycloalkyl,
e) a carbonyl group which is bonded to an unsubstituted or substituted group selected from aryl, cycloalkyl and $C_1-C_6$ alkyl substituted with hydrogen or an unsubstituted or substituted group selected from aryl and cycloalkyl, and g) a sulfonyl group which is bonded to an unsubstituted or substituted group selected from aryl, cycloalkyl and $C_1$–$C_6$ alkyl substituted with hydrogen or an unsubstituted or substituted group selected from aryl and cycloalkyl;

$R^5$ is independently selected from hydrogen, $C_1$–$C_6$ alkyl and aryl;

$R^6$ is independently selected from $C_1$–$C_6$ alkyl and aryl;

Z is $H_2$;

m is 0, 1 or 2, provided that m is 0 when $R^5$=hydrogen;

n is 0, 1, 2, 3 or 4; and t is 3;

or a pharmaceutically acceptable salt thereof.

5. A compound which inhibits farnesyl-protein transferase which is:

N-[2(R)-Amino-3-mercaptopropyl]-L-proline-2,3-dichlorobenzylamide

N-[2(R)-Amino-3-mercaptopropyl]-L-proline-1-naphthylmethyl amide

N-[2(R)-Amino-3-mercaptopropyl]-L-3-trans-ethylproline-2,3-dichlorobenzamide

N-[2(R)-Amino-3-mercaptopropyl]-D-3-trans-ethylproline-2,3-dichlorobenzamide

N-[2(R)-Amino-3-mercaptopropyl]-L-3-cis-ethylproline-2,3-dichlorobenzamide

N-[2(R)-Amino-3-mercaptopropyl]-D-3-cis-ethylproline-2,3-dichlorobenzamide

N-[2(R)-Amino-3-mercaptopropyl]-L-3-trans-ethylproline-1-naphthylmethyl amide

N-[2(R)-Amino-3-mercaptopropyl]-D-3-trans-ethylproline-1-naphthylmethyl amide

N-[2(R)-Amino-3-mercaptopropyl]-L-proline-2,3-dimethylphenyl amide

N-[2(R)-Amino-3-mercaptopropyl]-L-3-trans-ethylproline-2,3-dimethylphenyl amide; or N-[2(R)-Amino-3-mercaptopropyl]-D-3-transoethylproline-2,3-dimethylphenyl amide or a pharmaceutically acceptable salt thereof.

6. The compound according to claim 5 which inhibits farnesyl-protein transferase which is:

N-[2(R)-Amino-3-mercaptopropyl]-L-3-trans-ethylproline-2,3-dichlorobenzamide

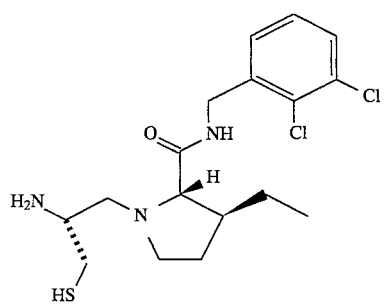

or a pharmaceutically acceptable salt thereof.

7. The compound according to claim 5 which inhibits farnesyl-protein transferase which is:

N-[2(R)-Amino-3-mercaptopropyl]-L-3-cis-ethylproline-2,3-dichlorobenzamide

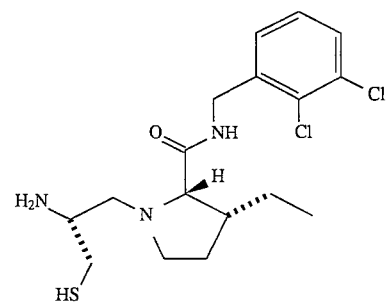

or a pharmaceutically acceptable salt thereof.

8. The compound according to claim 5 which inhibits farnesyl-protein transferase which is:

N-[2(R)-Amino-3-mercaptopropyl]-L-3-trans-ethylproline-1-naphthylmethyl amide

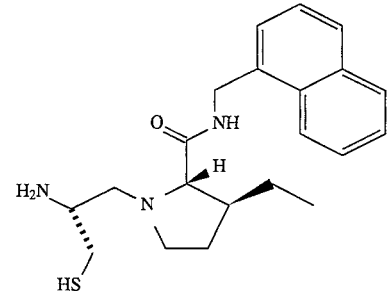

or a pharmaceutically acceptable salt thereof.

9. The compound according to claim 5 which inhibits farnesyl-protein transferase which is:

N-[2(R)-Amino-3-mercaptopropyl]-L-3-trans-ethylproline-2,3-dimethylphenyl amide

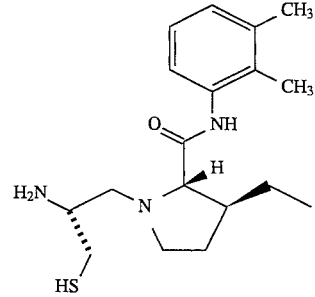

or a pharmaceutically acceptable salt thereof.

10. A pharmaceutical composition comprising a pharmaceutical carder, and dispersed therein, a therapeutically effective amount of a compound of claim 1.

11. A pharmaceutical composition comprising a pharmaceutical carrier, and dispersed therein, a therapeutically effective amount of a compound of claim 2.

12. A pharmaceutical composition comprising a pharmaceutical carrier, and dispersed therein, a therapeutically effective amount of a compound of claim 5.

13. A method for inhibiting farnesylation of Ras protein which comprises administering to a mammal in need thereof a therapeutically effective amount of the composition of claim 10.

14. A method for inhibiting farnesylation of Ras protein which comprises administering to a mammal in need thereof a therapeutically effective amount of the composition of claim 11.

15. A method for inhibiting farnesylation of Ras protein which comprises administering to a mammal in need thereof a therapeutically effective amount of the composition of claim 12.

16. A method for treating cancer which comprises administering to a mammal in need thereof a therapeutically effective amount of a composition of claim 10.

17. A method for treating cancer which comprises administering to a mammal in need thereof a therapeutically effective amount of a composition of claim 11.

18. A method for treating cancer which comprises administering to a mammal in need thereof a therapeutically effective amount of a composition of claim 12.

* * * * *

UNITED STATES PATENT AND TRADEMARK OFFICE
CERTIFICATE OF CORRECTION

PATENT NO. : 5,491,164
DATED : February 13, 1996
INVENTOR(S) : S. Jane deSolms, et al It is certified that error appears in the above-indentified patent and that said Letters Patent is hereby corrected as shown below:

On title page, item [75] entitled "Inventors," , Samuel J. Graham should read Samuel L. Graham.

At Column 24, in Claim 2, line 66, please delete the word --The -- and insert the word -- A -- in its place.

At Column 26, in Claim 3, line 31, please delete the word --The -- and insert the word -- A -- in its place.

At Column 30, in Claim 10, line 52, please delete the word --carder -- and insert the word -- carrier -- in its place.

Signed and Sealed this

Twenty-eighth Day of May, 1996

Attest:

BRUCE LEHMAN

*Attesting Officer*     *Commissioner of Patents and Trademarks*